(12) United States Patent
Davenport

(10) Patent No.: US 8,685,096 B2
(45) Date of Patent: Apr. 1, 2014

(54) LUMBAR FUSION DEVICE

(75) Inventor: Alan S Davenport, Flowery Branch, GA (US)

(73) Assignee: Amendia, Inc., Marietta, GA (US)

( * ) Notice: Subject to any disclaimer, the term of this patent is extended or adjusted under 35 U.S.C. 154(b) by 150 days.

(21) Appl. No.: 13/215,503

(22) Filed: Aug. 23, 2011

(65) Prior Publication Data

US 2013/0053963 A1 Feb. 28, 2013

(51) Int. Cl.
*A61F 2/44* (2006.01)

(52) U.S. Cl.
USPC ........................................... 623/17.11

(58) Field of Classification Search
USPC ................ 623/17.11–17.16; 606/248–249
See application file for complete search history.

(56) References Cited

U.S. PATENT DOCUMENTS

| | | | |
|---|---|---|---|
| 5,390,683 A * | 2/1995 | Pisharodi | 128/898 |
| 5,531,792 A * | 7/1996 | Huene | 623/23.47 |
| 5,554,191 A * | 9/1996 | Lahille et al. | 623/17.11 |
| 5,645,589 A * | 7/1997 | Li | 606/60 |
| 5,843,127 A * | 12/1998 | Li | 606/232 |
| 5,980,522 A | 11/1999 | Koros et al. | |
| 6,022,373 A * | 2/2000 | Li | 606/232 |
| 6,126,689 A | 10/2000 | Brett | |
| 6,129,762 A * | 10/2000 | Li | 623/13.11 |
| 6,149,669 A * | 11/2000 | Li | 606/232 |
| 6,176,882 B1 * | 1/2001 | Biedermann et al. | 623/17.15 |
| 6,190,414 B1 | 2/2001 | Young et al. | |
| 6,214,050 B1 * | 4/2001 | Huene | 623/17.15 |
| 6,302,914 B1 | 10/2001 | Michelson | |
| 6,409,766 B1 * | 6/2002 | Brett | 623/17.16 |
| 6,436,119 B1 | 8/2002 | Erb et al. | |
| 6,458,159 B1 | 10/2002 | Thalgott | |
| 6,478,800 B1 | 11/2002 | Fraser et al. | |
| 6,520,967 B1 | 2/2003 | Cauthen | |
| 6,520,991 B2 * | 2/2003 | Huene | 623/17.11 |
| 6,562,074 B2 | 5/2003 | Gerbec et al. | |
| 6,572,653 B1 | 6/2003 | Simonson | |
| 6,575,973 B1 * | 6/2003 | Shekalim | 606/62 |
| 6,669,699 B2 | 12/2003 | Ralph et al. | |
| 6,723,126 B1 | 4/2004 | Berry | |
| 6,770,094 B2 | 8/2004 | Fehling et al. | |
| 6,855,166 B2 | 2/2005 | Kohrs | |
| 7,087,055 B2 * | 8/2006 | Lim et al. | 606/99 |
| 7,445,636 B2 | 11/2008 | Michelson | |
| 7,691,113 B2 * | 4/2010 | Ortiz et al. | 606/139 |
| 7,857,854 B2 * | 12/2010 | Sweeney | 623/17.11 |

(Continued)

FOREIGN PATENT DOCUMENTS

| | | |
|---|---|---|
| WO | 0154598 | 8/2001 |
| WO | 2005048856 | 6/2005 |
| WO | 2010108333 | 9/2010 |

*Primary Examiner* — Ellen C Hammond
*Assistant Examiner* — Jacqueline Johanas
(74) *Attorney, Agent, or Firm* — David L King

(57) ABSTRACT

A lumbar fusion implant device has a pair of first and second body structures. The first body structure has a pair of appendages with enlarged rounded ends, the appendages projecting from the opposite sides of the first body structure. Similarly, the second body structure has a pair of appendages with enlarged rounded ends with the appendages projecting from opposite sides of the second body structure. Each of the enlarged ends of the appendages fit into sockets on an opposite first or second body structure and when the first and second body structures are longitudinally connected by a threaded fastener, tightening of the fastener moves the first and second body structures closer together expanding radially outwardly each appendage.

10 Claims, 5 Drawing Sheets

(56) References Cited

U.S. PATENT DOCUMENTS

| | | |
|---|---|---|
| 7,909,825 B2 * | 3/2011 | Saravia et al. .................. 606/66 |
| 7,951,180 B2 | 5/2011 | Moskowitz et al. |
| 7,959,652 B2 | 6/2011 | Zucherman et al. |
| 7,976,579 B2 * | 7/2011 | Francis ...................... 623/17.11 |
| 8,097,018 B2 * | 1/2012 | Malandain et al. ........... 606/246 |
| 8,197,514 B2 * | 6/2012 | Maas et al. .................... 606/248 |
| 2002/0068977 A1 | 6/2002 | Jackson |
| 2002/0138146 A1 | 9/2002 | Jackson |
| 2002/0143401 A1 | 10/2002 | Michelson |
| 2002/0161444 A1 | 10/2002 | Choi |
| 2004/0088054 A1 | 5/2004 | Berry |
| 2004/0133204 A1 | 7/2004 | Davies |
| 2004/0133280 A1 | 7/2004 | Trieu |
| 2005/0021041 A1 | 1/2005 | Michelson |
| 2005/0070934 A1 * | 3/2005 | Tanaka et al. ................. 606/153 |
| 2005/0143827 A1 | 6/2005 | Globerman et al. |
| 2005/0203625 A1 | 9/2005 | Boehm et al. |
| 2005/0228391 A1 | 10/2005 | Levy et al. |
| 2005/0278026 A1 | 12/2005 | Gordon et al. |
| 2006/0224241 A1 | 10/2006 | Butler et al. |
| 2007/0225807 A1 | 9/2007 | Phan et al. |
| 2007/0255409 A1 | 11/2007 | Dickson et al. |
| 2007/0270834 A1 | 11/2007 | Bruneau et al. |
| 2007/0282443 A1 | 12/2007 | Globerman et al. |
| 2008/0027438 A1 * | 1/2008 | Abdou ............................ 606/61 |
| 2008/0058934 A1 | 3/2008 | Malandain et al. |
| 2008/0103573 A1 | 5/2008 | Gerber |
| 2008/0221685 A9 | 9/2008 | Altarac et al. |
| 2008/0262617 A1 | 10/2008 | Froehlich et al. |
| 2008/0269758 A1 | 10/2008 | Baynham et al. |
| 2008/0300601 A1 * | 12/2008 | Fabian et al. ................... 606/90 |
| 2008/0312741 A1 | 12/2008 | Lee et al. |
| 2009/0171461 A1 * | 7/2009 | Conner et al. ............. 623/17.11 |
| 2009/0270918 A1 | 10/2009 | Attia et al. |
| 2009/0270989 A1 * | 10/2009 | Conner et al. ............. 623/17.16 |
| 2009/0292316 A1 | 11/2009 | Hess |
| 2010/0004688 A1 * | 1/2010 | Maas et al. .................... 606/248 |
| 2010/0168794 A1 | 7/2010 | Weng et al. |
| 2010/0268341 A1 | 10/2010 | Dvorak et al. |
| 2010/0305705 A1 * | 12/2010 | Butler et al. ............... 623/17.16 |
| 2011/0082556 A1 | 4/2011 | Duggal et al. |
| 2012/0004732 A1 * | 1/2012 | Goel et al. ................. 623/17.16 |

\* cited by examiner

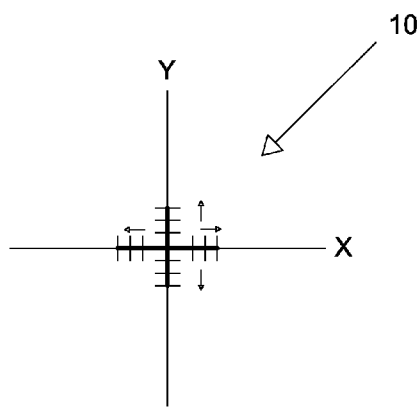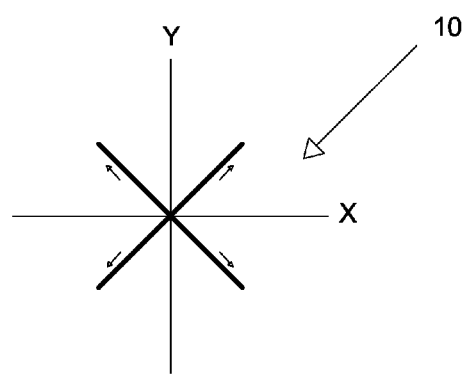
Figure 4A                    Figure 4B

LUMBAR FUSION DEVICE

TECHNICAL FIELD

The present invention relates generally to interbody spinal implants for insertion into an implantation space in the spine, and in particular to expandable interbody lumbar fusion implants for the immobilization of adjacent vertebrae for placement at least in part in the disk space between adjacent vertebral bodies in the space previously occupied by disc material.

BACKGROUND OF THE INVENTION

Expandable spinal implants have height raising capabilities that are utilized once the implant is initially positioned. Such height raising capability may be utilized within the spine anteriorly, posteriorly, or both and to various extents, respectively to raise the front or back of the implant. More particularly, such implants have upper and lower surfaces of upper and lower portions that in an insertion position are collapsed relative to one another and in a deployed position are spaced further away from one another than in the collapsed position.

Expandable implants offer the advantage of allowing for the placement of a potentially larger implant through a smaller opening in a patient's body. One of the first expandable spinal implants allowing for the growth of bone from vertebral body to vertebral body through the implant was invented by Michelson which is disclosed in U.S. Pat. No. 5,776,199, filed Jun. 28, 1988.

The prior art expandable interbody spinal implants preferably were inserted from an anterior approach to the spine, an approach posterior to the vertebral transverse processes, or to either side of the spinal midline in pairs. Such expandable implants are adapted to increase in height at their leading ends or at their trailing ends from a collapsed state to an expanded state for the purpose of increasing spinal lordosis at that interspace. During installation of expandable interbody spinal implants, it is desirable that the surgeon have the ability to precisely control the implant with the appropriate instruments and methods to load the implant with appropriate bone growth promoting material, to insert the implant into the implantation space, to deploy the implant to a final expanded state, and to further load the implant with bone growth material if so desired.

The technology of these prior art devices is such that the implant when expanded can be anchored into the adjacent vertebra similar to how drywall anchors used in building construction expand as a threaded fastener is screwed into the anchor. To avoid turning or rotation saw toothed edges are provided on the exterior surfaces which embed themselves into the bone.

Also known in the prior art are expandable interbody spinal implants that are circumferentially expandable at one of their leading or trailing ends to expand both the height and the width of the implant. Such implants have an expansion mechanism that is moved from the trailing end through the interior of the implant to reach the leading end to expand the implant. Any bone growth material present within the interior of the implant would be forced out of the interior of the implant by the expansion mechanism passing therethrough. Accordingly, such implants cannot be effectively preloaded with bone growth promoting material prior to expansion of the implant.

There exists a need for a circumferentially expanding implant that is stable when positioned and is substantially hollow and substantially devoid of any elaborate or substantial space occupying expansion mechanism to permit preloading of the implant with bone growth promoting material prior to expansion of the implant. The expansion mechanism should not interfere with the capacity to compressively load osteogenic material such as bone or any other suitable material through the length of the implant and to have it extrude from the implant. The extrusion of the osteogenic material from the implant provides an increased volume of osteogenic material over a greater surface area of the adjacent vertebral bodies adjacent the disc space to be fused and beyond the surface area of contact of the implant to the vertebral bodies themselves. Surrounding the implant itself with additional fusion promoting substances in contact with the adjacent vertebral bodies may enhance the fusion process.

SUMMARY OF THE INVENTION

A lumbar fusion device has a pair of first and second body structures. The first body structure has a pair of appendages with enlarged rounded ends, the appendages projecting from the opposite sides of the first body structure. Similarly, the second body structure has a pair of appendages with enlarged rounded ends with the appendages projecting from opposite sides of the second body structure. Each of the enlarged ends of the appendages fit into sockets on an opposite first or second body structure and when the first and second body structures are longitudinally connected by a threaded fastener, tightening of the fastener moves the first and second body structures closer together expanding radially outwardly each appendage. Each appendage preferably has a bowed curvature. The first or second body structures have a central portion, the central portion of one of the first or second body structure fitting inside the central portion of the other in a telescoping configuration. The central portions have an opening extending through the length of each central portion to accept the threaded fastener. One or both of the central openings being threaded to engage the fastener and tightening the fastener causes the pair of body structures to move closer to radially bend outwardly the appendages and loosening the fastener lowering the appendages reducing the curvature.

The sockets on each side of the first or second body structures are slotted to allow the enlarged round end of the appendage of an opposite body structure to slip into the socket. Also, the socket has a ramped or sloping curvature to facilitate the round end of the appendage to slip or move relative to the socket upon tightening the fastener.

BRIEF DESCRIPTION OF THE DRAWINGS

The invention will be described by way of example and with reference to the accompanying drawings in which:

FIGS. 4a and 4b are diagrammatic views of the lumbar fusion implant device shown in an unexpanded and expanded condition in a vertical and horizontal orientation.

DETAILED DESCRIPTION OF THE INVENTION

Figure 1:
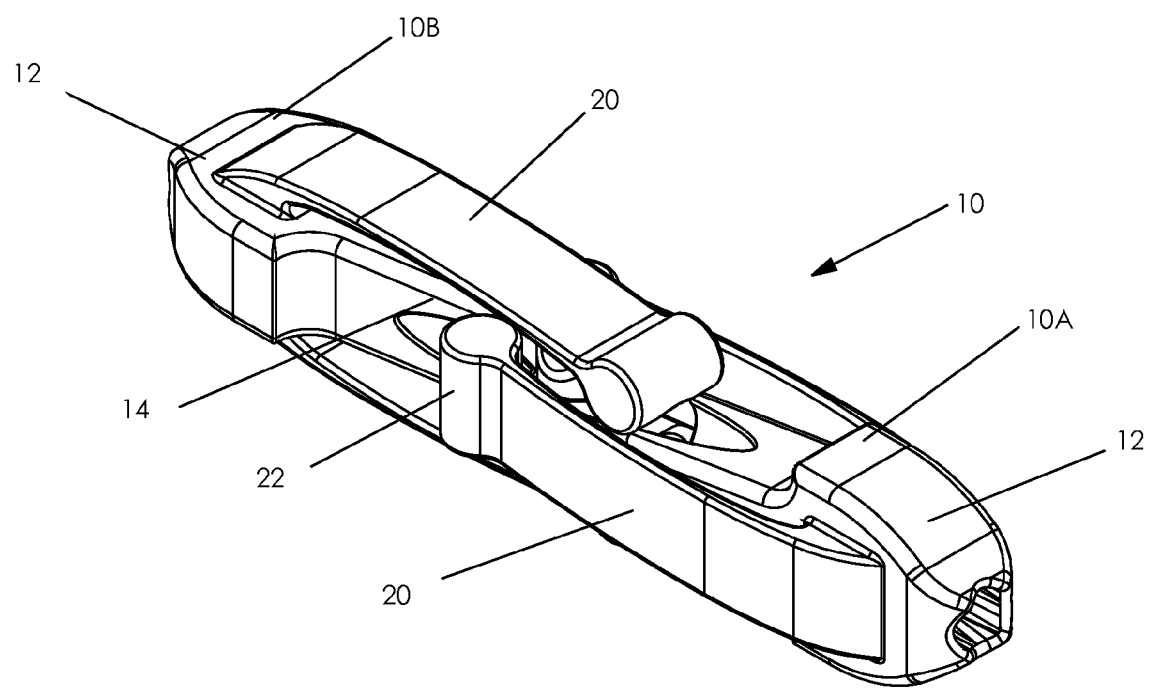
FIG. 1 is a perspective view of the improved lumbar fusion implant device made according to the present invention.

With reference to FIGS. 1, 2a, 2b and 3 a lumbar fusion implant device 10 is illustrated. The lumbar fusion implant device 10 as shown in FIG. 1 has a first body structure 10a and second body structure 10b joined as an assembly. The first and second body structures 10a and 10b are uniquely similar and adapted to fit and connect with the other body structure to form a cooperating implant device 10 that when a threaded fastener 40 is inserted into the device 10 and tightened, the device 10 longitudinally contracts along the axis of the screw 40 when tightened in such a fasten that appendages 20 integrally formed on each body structure 10a and 10b and connected to the other or opposite body structure are deformed bending outwardly and expanding the overall dimensions of the lumbar fusion device 10 in order to achieve an increased spacing between adjacent vertebrae when the device 10 is placed in between the vertebrae.

Figure 2A:
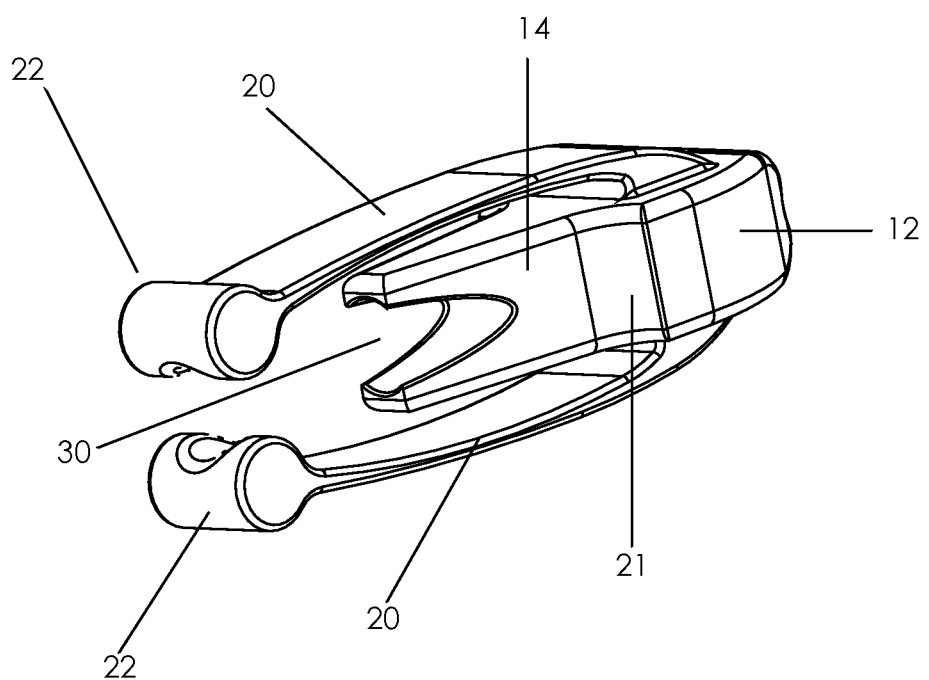
FIG. 2a is a perspective view of the first body structure.
Figure 2B:
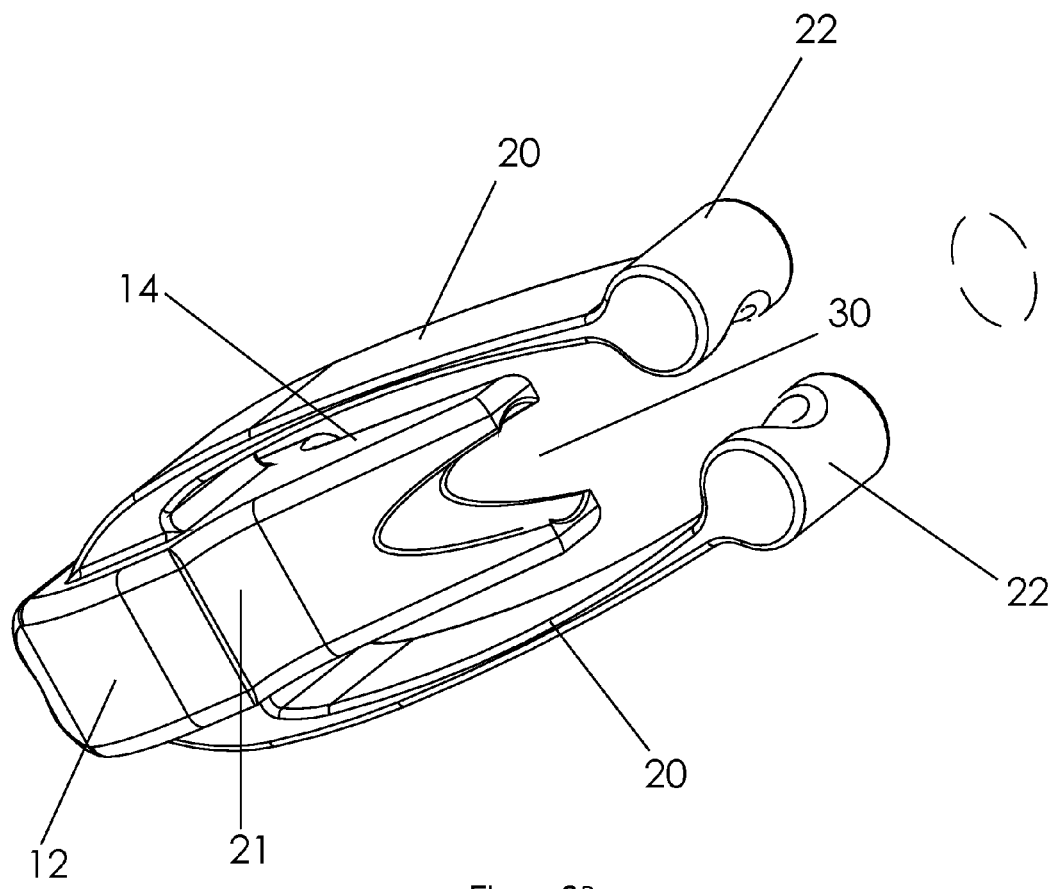
FIG. 2b is a perspective view of the second body structure.
Figure 3:
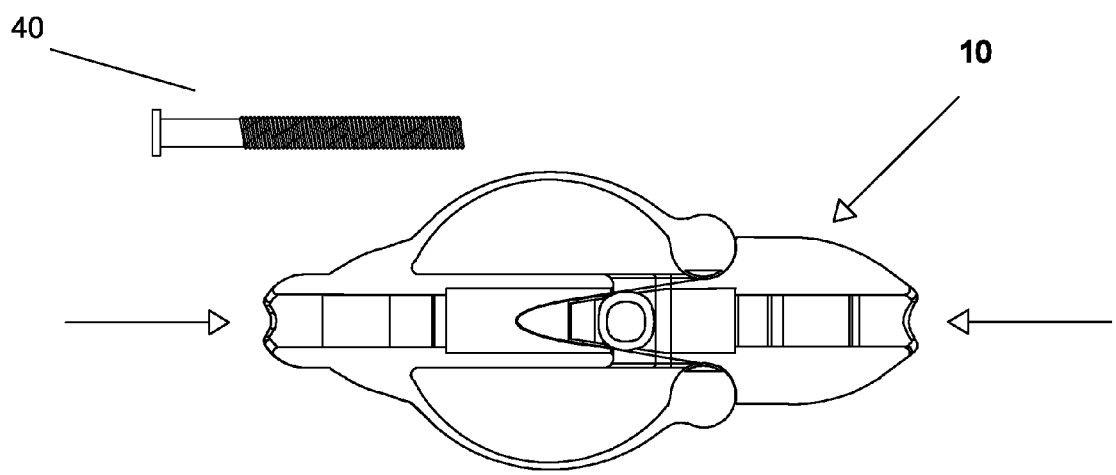
FIG. 3 is a side cross sectional view of the implant device taken along lines 3-3 of FIG. 1.

With reference to FIG. 2a, the first body structure 10a is shown having an enlarged end 12 from which a pair of appendages or arms 20 project outwardly in a curvilinear fashion. These appendages 20 terminate at a distal end with a rounded cylindrical end 22 which forms a rounded end 22 of the appendage 20. As shown, the rounded end 22 is cylindrical, alternatively the rounded end 22 could be spherical. Interposed between the appendages 20 and extending from the enlarged end 12 is a central portion 14. As shown, the central portion 14 has an opening hole 30 through it which allows the threaded fastener 40 to pass. The second body structure 10b is identical to the first body structure 10a with several minor exceptions. As shown in FIG. 2b, the second body structure 10b has a similar central portion 16 that is adapted to slide over the central portion 14 of the first body structure 10a and has a threaded hole 32 to which the fastener 40 can be secured. As shown in FIG. 3, the fastener 40 has a smooth shoulder shank for sliding into the first body structure 10a and a threaded end for engaging the second body structure 10b and when the fastener 40 is secured the tightening of the threaded fastener 40 enables the first body structure 10a to move inwardly closing the relative distance between the two body structures 10a and 10b in such a fashion that the interlocking appendages 20 will be curved or bent. To achieve this curving or bending each of the body structures 10a and 10b has a socket 21 adjacent the enlarged end 22. This socket 21 is adapted to accept the large rounded end 22 of the appendage 20 and when placed into the socket 21 secures the end 22 in such a fashion that it can only move in a direction to put pressure on the appendage 20 causing it to deform or bend outwardly as the two body structures 10a and 10b are moved closer together. This ability to expand the appendages 20 outwardly to increase their overall radial dimension relative to each other enables the device 10 to enlarge both in a vertical and a lateral position when the implant is placed between the adjacent vertebrae in such a fashion that the device appears to have a plus (+) configuration. In this fashion as illustrated diagrammatically in FIG. 4, as the threaded fastener tightens, the overall length of the device 10 shortens and the appendages 20 flex outwardly both in the lateral direction and the vertical direction as illustrated in the diagrammatic view of FIG. 4a. Prior to expanding the appendages 20, the exemplary device 10 is only 8 mm in width and height, but as the device 10 is pulled together it is expanded and the cylindrical or rounded ends 22 move along the ramped surfaces and the appendages 20 are bent enlarging to 16 mm in width and height doubling the size of the device 10.

While the lumbar fusion implant device 10 is shown wherein a vertical expansion is achieved and a lateral expansion is achieved by the lateral appendages during tightening of the device 10 it must be appreciated that the device can be tilted 45 degrees upon assembly in such a fashion that the appendages form an X configuration between the adjacent vertebrae, as shown in FIG. 4b. In this fashion, the lumbar fusion implant device 10 can be tightened causing the appendages 20 to move vertically and horizontally upward along a 45 degree angle path as they expand on both sides of the upper surface of a vertebra and on both sides of a lower surface of an adjacent vertebra. In this "x" configuration some pressure is put on the vertebrae as the device is expanding, however it is a very stable configuration in that the implant cannot rotate or turn in any fashion once it is implanted in an X configuration. While this rotation is considered a minor inconvenience it is something to be considered when working on a very active patient or one which requires a lot of mobility. In this fashion the device 10 can be located so that the appendages 20 can move sufficiently to both space the adjacent vertebrae and to allow a maximum amount of spinal bone grafting implant material to be positioned between the appendages 20 and the central portions 14 or 16 of the two body structures 10a and 10b. An advantage of the present invention is that the two moving parts ability to slide relative to each other in a telescoping fashion enables the device 10 to take an extremely low profile on insertion and to expand dramatically outwardly upon tightening of the threaded fastener 40. Furthermore, the device 10 can be easily loaded with bone graft material in a large quantity around the central portions 14 and 16 and between the appendages 20 to increase the likelihood of rapid fusion of the bones creating a quicker healing time for the patient due to the large amount of bone graft material that can be surrounding the lumbar fusion device 10 with the flexible expandable appendages 20.

As further shown, the sockets 21 for accepting the enlarged ends 22 of the appendages 20 are designed to have a slight curvature so that the cylindrical or rounded ends 22 can freely move relative to the structure 10a or 10b as it is being tightened. This ability to slide against the socket 21 enables the device 10 to flex freely without binding. This is important because the device 10 needs to be able to be tightened without moving significantly relative to the vertebrae during the implant procedure. Furthermore, when one compares the first body structure 10a to the second body structure 10b it is important to note that they are virtually identical with the exception of the overlapping central portions 14 and 16 and the pass through opening or holes 30, 32 that extends longitudinally to allow the threaded fastener 40 to connect one body part to the other enabling the device 10 to be moved and expanded. On assembly it is important to note that the second body structure 10b is oriented with the large end 12 rotated approximately 90 degrees relative to the enlarged end 12 of the opposite body structure 10a. This rotation of the body structures 10a and 10b enables the device 10 to freely be assembled as shown allowing the appendages 20 to intersect the directionally opposite sockets 21 on each body structure 10a or 10b which are oriented approximately 180 degrees apart within a respective body structure 10a or 10b which are designed to be rotated such that on assembly the two devices have an appendage at each 90 degree location about the device 10.

As previously discussed, the device 10 can be positioned so that the implant is oriented with a vertical extending appendages 20 and a horizontal extending appendages to achieve a maximum amount of vertical or lateral displacement of the device 10 or alternatively can be implanted in an X configuration allowing the device 10 to anchor itself securely in a more stable condition. As shown the appendages 20 are illustrated having smooth outer surfaces, however it is contemplated that these bone contacting surfaces can be serrated or provided with bone gripping texturing 20A as shown in FIG. 3 to facilitate securing the appendages 20 relative to the adjacent bone so that it does not slip or move upon implantation. While it is possible for the device to be altered or modified in several characteristics, one of which would be enclosing the open socket 21 within each body structure 10a or 10b on one side so that the device 10 can only fit in one direction and not slip out during a tightening procedure to help secure the device 10 so that the appendages 20 provide additional lateral support so that the two body structures 10a and 10b cannot to slip relative to each other. In addition to the central portions 14 and 16 which also prevent this type of rotation, the device 10 also alternatively can change or modify the shape of the appendages 20 slightly providing an enlarged flattened area in the central or mid region allowing the device 10 to take a more stable anchoring position on implantation. These and other variations are considered well within the scope of the present invention. What is important is that the device 10 has two cooperating parts 10a and 10b which upon tightening the screw 40 allow the projecting appendages 20 to flex because they are initially curved slightly outwardly this flexure causes additional flexure bowing the appendages 20 in a fashion similar to a crossbow in such a fashion that the device 10 moves the appendages 20 outwardly to achieve the proper spacing of the vertebrae. The advantage of the present invention is that this is accomplished in a central or mid portion of the device 10 between the two body structures 10a and 10b this is an advantage in that the surgeon when placing the implant can position it in such a fashion that the lift occurs centrally and not at one end of the implant of the device as is common practice in almost all spinal implants used today. While it is argued that providing an increasing space at one end or the other of an implant is advantageous to the surgeon, it is actually detrimental to the patient in the following regard. The patient's vertebrae are designed to rotate slightly fore and aft and by providing a centrally expanding interspinous implant with a curvilinear lift pattern as illustrated the implant device 10 allows the patient's vertebrae to be more flexible and less rigid while still maintaining a sufficient space to relieve the pain associated with the problem being corrected. The device 10, during the healing process as the bones are fusing, enables the vertebrae to be effectively positioned in a way that is more common to the natural spinal structure and the patient will have a much greater degree of comfort with the insertion of this type of an implant device.

A second advantage is that the surgeon knows that the central location of the implant device is precisely where the elevation occurs. In the current practice, where an end is elevated he does the spacing on a normally linear increasing inclination. This effectively moves the spinal implant device in such a fashion that only the ends can achieve the needed spacing. The present invention by centrally locating the location of increasing distance between the appendages 20 ensures that the surgeon knows precisely where the lifting between the vertebrae is occurring this location does not move relative to the lumbar fusion device 10 even though the implant device 10 is longitudinally compressing in its overall longitudinal length as the threaded fastener tightens. This is true because the location of maximum deflection is occurring at a central location that does not shift, but moves equally on each side of the body structure 10a and 10b in such a fashion that as the two parts come closer together the maximum deflection is constant in a singular plane. This is a huge advantage for the surgeon and provides a very positive way in which an implant can be positioned achieving a greater amount of deflection in a rather small and convenient sized device.

As previously mentioned, the device 10 upon assembly provides a large amount of space between the appendages 20 and openings on all 90 degrees spacing between appendages 20. The space between the appendages 20 being the 90 degree space between each appendage provides a large amount of space for which bone graft material and other biologically based material can be inserted around the device 10. This is a huge advantage over the present prior art implant devices which if they have a threaded fastener moving it through the center portion with almost no room or space provided for putting bone graft material. The present invention provides a large amount of volumetric space in which to put large quantities of bone graft material. This is believed to be beneficial in that it will help accelerate the healing and the acceptance and fusion of the adjacent vertebrae.

As shown the present device can be made out of titanium, carbon fiber material, PEEK or any other implantable suitable material as long as appendages 20 are provided with a sufficient spring like strength such that they can maintain their ability to flex outwardly and to lift the adjacent vertebrae as required for the procedure.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A lumbar fusion interspinous implant device comprises:
a pair of first and second body structures;
the first body structure having a pair of outwardly curved appendages with enlarged rounded ends and an initial outward curvature, the appendages projecting from the opposite sides of the first body structure;
the second body structure having a pair of outwardly curved appendages with enlarged rounded ends and an initial outward curvature, the appendages projecting from opposite sides of the second body structure; and
wherein each of the enlarged ends of the appendages fit into sockets on an opposite first or second body structure, and the first and second body structures are longitudinally connected by a threaded fastener,
wherein tightening of the threaded fastener moves the first and second body structures closer together in a longitudinal direction, thereby placing the enlarged ends in contact with the sockets of the opposite body structure, wherein when the enlarged ends are in contact with the sockets the enlarged ends are prevented from further movement past the socket in the longitudinal direction in response to further tightening of the threaded fastener;
wherein the further tightening of the threaded fastener causes each appendage to deform and bend, thereby expanding radially outward in a central or mid portion of the device, the radially outward expansion increasing the distance between central locations on each appendage, said locations being spaced from the enlarged end;
wherein the distance increase between each appendage is greatest at the central location of each appendage to provide the centrally expanding interspinous implant device with a curvilinear lift pattern.

2. The lumbar fusion interspinous implant device of claim 1 wherein each appendage has a bowed curvature, and upon tightening, the threaded fastener causes additional flexure bowing of the appendages moving the appendages centrally outwardly at the central location of the appendages spaced from the enlarged ends.

3. The lumbar interspinous implant fusion device of claim 1 wherein the first and second body structures each have a central portion, the central portion of one of the first or second body structure fitting inside the central portion of the other in a telescoping configuration.

4. The lumbar fusion interspinous implant device of claim 3 wherein the central portions have an opening extending through the length of each central portion to accept the threaded fastener, one or both of the central openings being threaded to engage the fastener and tightening the fastener causes the pair of body structures to move closer to radially bend, outwardly increasing the outward curvature of the appendages and loosening the fastener lowers the appendages reducing the outward curvature of outwardly curved appendages.

5. The lumbar fusion interspinous implant device of claim 1 wherein the sockets on each side of the first or second body structures are slotted to allow the enlarged round ends of the appendages of an opposite body structure to slip into the sockets.

6. The lumbar fusion interspinous implant device of claim 1 wherein the sockets have a ramped or sloping curvature to facilitate the enlarged rounded ends of the appendages to slip or rotate relative to the sockets upon tightening the fastener.

7. The lumbar fusion interspinous implant device of claim 1 wherein the location of the greatest distance increase between each appendage occurs in a single plane and does not shift relative to either the first or second body structure as the implant device is longitudinally compressed as the threaded fastener is tightened.

8. The lumbar fusion interspinous implant device of claim 7 wherein the greatest distance increase between each appendage occurs equally in a singular plane.

9. The lumbar fusion interspinous implant device of claim 1 wherein the implant device is oriented with one pair of appendages extending vertically and the other pair of appendages extending horizontally.

10. The lumbar fusion interspinous implant device of claim 1 wherein the implant device is implanted in an "X" configuration.

* * * * *